Figure 1:
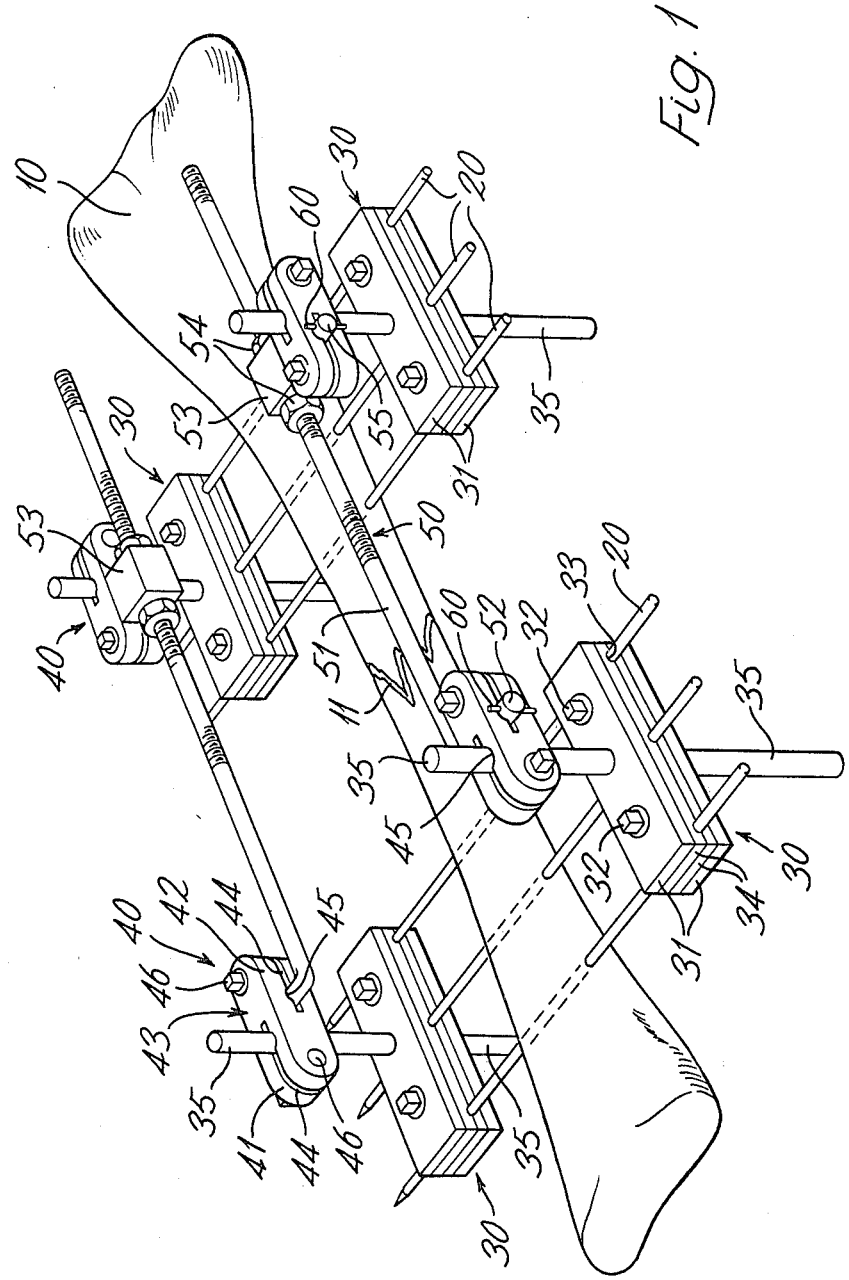

United States Patent [19]

Sayegh

[11] 4,349,017
[45] Sep. 14, 1982

[54] ORTHOPAEDIC APPARATUS

[76] Inventor: Antoine Y. Sayegh, Wexham Park Hospital, Wexham Road, Slough, Berkshire, England

[21] Appl. No.: 189,840
[22] PCT Filed: Apr. 2, 1979
[86] PCT No.: PCT/GB79/00055
§ 371 Date: Nov. 30, 1979
§ 102(e) Date: Nov. 26, 1979
[87] PCT Pub. No.: WO79/00866
PCT Pub. Date: Nov. 1, 1979

[30] Foreign Application Priority Data

Mar. 31, 1978 [GB] United Kingdom ............. 12608/78
Apr. 28, 1978 [GB] United Kingdom ............. 17051/78

[51] Int. Cl.³ .......................... A61F 5/04; A61B 17/18
[52] U.S. Cl. ............................. 128/92 A; 128/92 EB
[58] Field of Search ............. 128/92 A, 92 EB, 92 E, 128/92 R, 419 F; 408/241 B, 241 G

[56] References Cited

U.S. PATENT DOCUMENTS

| | | | |
|---|---|---|---|
| 2,238,870 | 4/1941 | Haynes | 128/92 A |
| 2,391,537 | 12/1945 | Anderson | 128/92 A |
| 4,061,437 | 12/1977 | Stranger et al. | 408/241 G |
| 4,135,505 | 1/1979 | Day | 128/92 A |

FOREIGN PATENT DOCUMENTS

| | | | |
|---|---|---|---|
| 849147 | 1/1977 | Belgium | 128/92 A |
| 2553782 | 6/1977 | Fed. Rep. of Germany | 128/92 A |
| 2718515 | 11/1977 | Fed. Rep. of Germany | 128/92 A |
| 851028 | 1/1940 | France | 128/92 A |
| 1577235 | 6/1969 | France | 128/92 A |

OTHER PUBLICATIONS

PCT/GB79/00055, The Tibial Fram, A. Y. Sayegh.
PCT Gazette, Secton 1, No. 22/1979, p. 914; Gazette entry of PCT/GB79/00055.

Primary Examiner—Kyle L. Howell
Assistant Examiner—C. W. Shedd
Attorney, Agent, or Firm—Cushman, Darby & Cushman

[57] ABSTRACT

The invention concerns orthopaedic fracture apparatus involving adjustable assemblies of rods and coupling mechanisms connected to different parts of a fractured bone whereby the bone can be manipulated to and stabilized in a desired configuration. The invention provides, for such apparatus, coupling mechanisms each including a pair of clamps which are independently operable, rigidly interconnected, and have guides to secure rods and the like in mutually perpendicular directions whereby manipulation can be effected selectively in mutually perpendicular planes by loosening corresponding first clamps or second clamps of these couplings. The geometry of the remainder of the apparatus should be appropriate to this function. For this purpose one form of bone pin connection assembly clamps a set of pins in a parallel coplanar array and has an orthogonal post for a coupling mechanism, and another form of such connection assembly involves a curved plate conforming to a limb and with mutually perpendicular tubular projections from its convex surface, these projections serving as pin guide/clamp sleeves and coupling posts.

3 Claims, 9 Drawing Figures

ORTHOPAEDIC APPARATUS

Various proposals have been made for orthopaedic fracture fixation apparatus which involve adjustable assemblies of rods and coupling mechanisms connected to different parts of a fractured bone whereby the bone can be manipulated to and stabilised in a desired configuration. Some of the benefits of such apparatus are that patients can be quickly mobilised and so require less physiotherapy, wounds associated with fractures can be readily inspected and treated due to the absence of a plaster cast, and the bone can be subjected to compression or distraction by the apparatus.

The more versatile forms of such apparatus in terms of adjustment capability normally involve coupling mechanisms which, when loosened, allow the rods or other members coupled thereby to undergo relative movement in many if not all directions. This is disadvantageous in rendering difficult the control of at least the finer, final manipulation of bone fragments into a desired positional relationship.

An object of the present invention is to obviate this last difficulty and to this end there is provided orthopaedic fracture fixation apparatus of the general kind in question comprising coupling mechanisms each including a pair of clamps which are independently operable, rigidly interconnected, and have guides to secure elongate members in predetermined, mutually perpendicular directions. In addition, the overall geometry of the apparatus should be such as to comprise at least two like clamp assemblies each having guides to secure at least two bone pins in individually predetermined directions, and each having at least one post projecting therefrom in a predetermined angular relationship with said guides, there being at least four of said posts locatable as two pairs on opposite sides of a bone fracture by appropriate positioning of said clamp assemblies; at least two longitudinally adjustable rod mechanisms each for location to extend between a different pair of corresponding ones of said four posts on respectively opposite sides of said fracture; and at least four of said coupling mechanisms, each located with its two clamps respectively securing adjacent portions of one of said posts and the associated one of said rod mechanisms.

This apparatus is operable to allow selective adjustment of its overall configuration in two mutually perpendicular planes as will be appreciated more fully hereinafter.

In a first developed form of the invention which is currently undergoing clinical trials, the clamp assemblies each secure bone pins in a parallel coplanar array, and have a post perpendicular to the respective array plane. In a second form of the invention under development the clamp assemblies each comprise a curved or similarly shaped plate conforming generally to a limb portion profile, such plate having at least two mutually perpendicular tubular projections therefrom to serve as bone pin guides/clamp sleeves and as posts.

Figure 2:
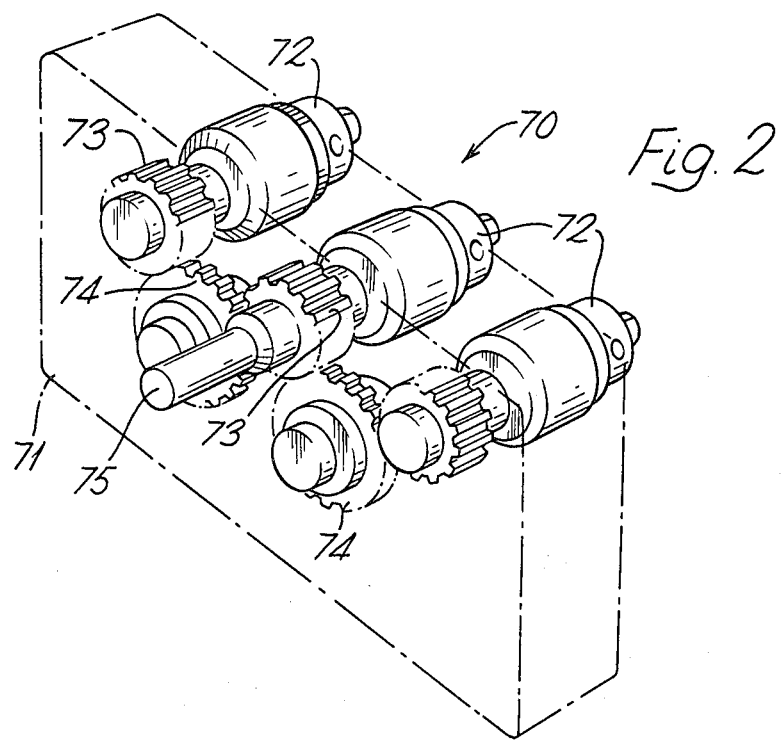
Figure 3:
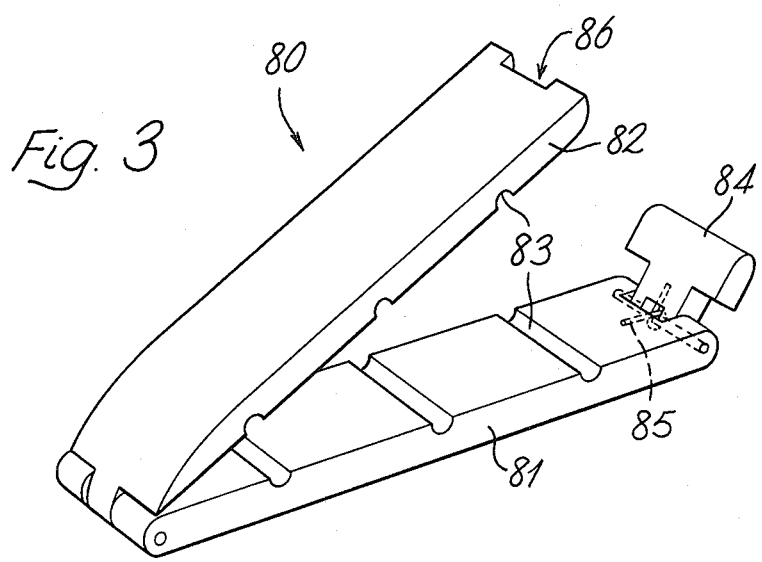
Figure 4A:
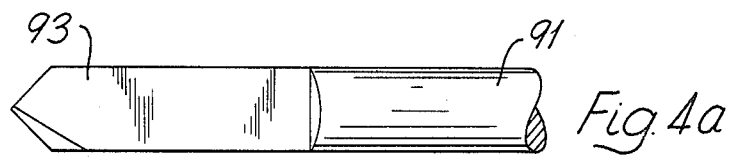
Figure 4B:
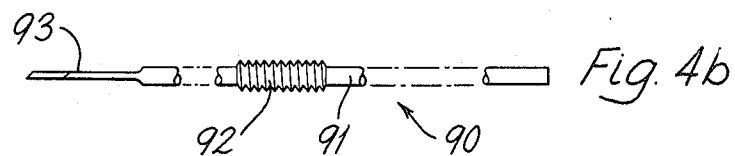
Figure 5A:
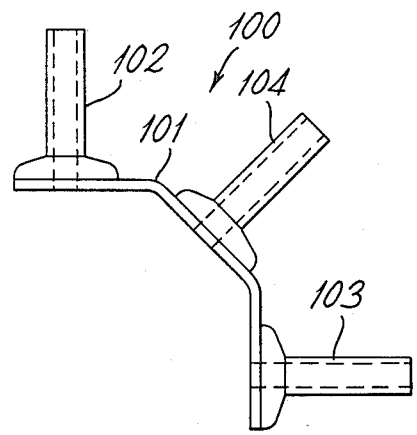
Figure 5B:
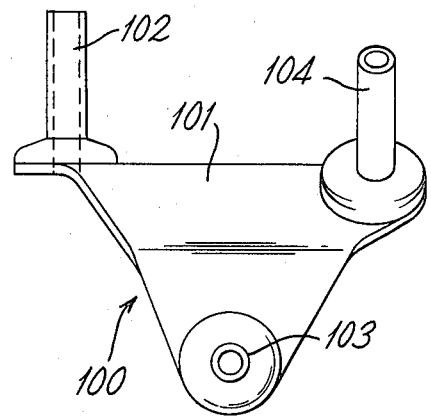
Figure 5C:
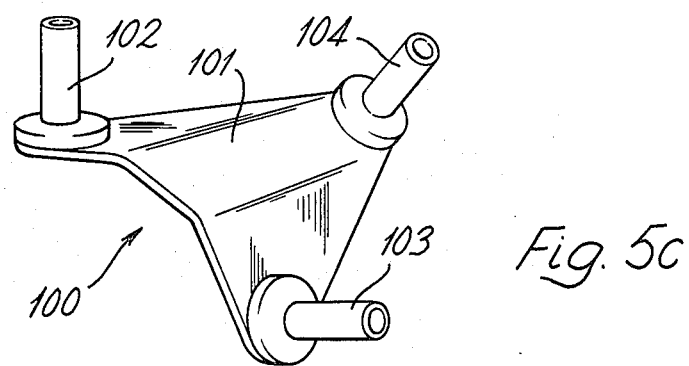
Figure 6:
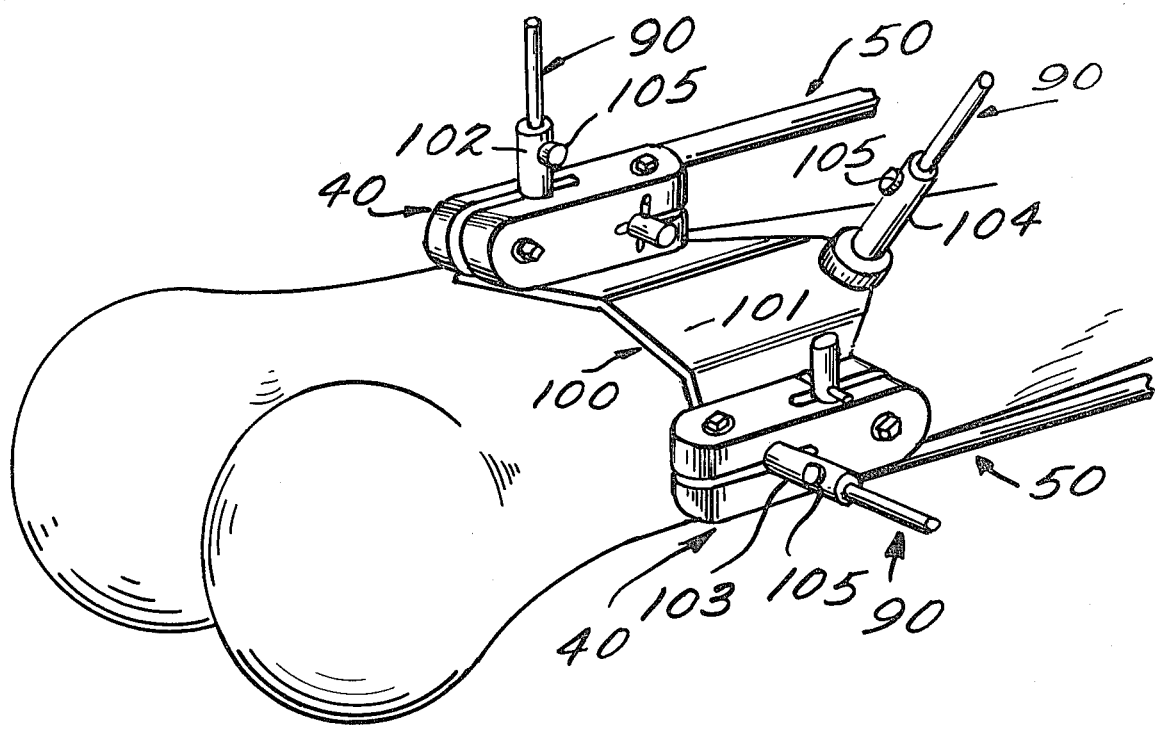

In order that the invention may be more fully understood, the same will now be described, by way of example, with reference to the accompanying drawings, in which:

FIG. 1 schematically illustrates one embodiment of the proposed apparatus assembled in use;

FIG. 2 schematically illustrates a drill accessory preferred for use in insertion of the bone pins of FIG. 1;

FIG. 3 similarly illustrates a guide accessory preferred for use in association with the drill accessory of FIG. 2;

FIG. 4 respectively illustrates in different views (a) and (b) a preferred form of bone pin for use with the embodiment of FIG. 1;

FIG. 5 respectively illustrates in different views (a) and (c) another form of clamp mechanism from that of FIG. 1; and FIG. 6 illustrates the clamp mechanism of FIG. 5 assembled in use.

FIG. 1 shows an embodiment of the proposed apparatus assembled in use relative to a long bone 10, typically in the leg, having a fracture 11.

The apparatus is coupled in use to the bone by way of bone pins 20 which can be of known form. There should be at least two such pins, and preferably three, passing through the bone on each side of the fracture, as shown. Also, for the purposes of the apparatus of FIG. 1, the two sets of pins on the different sides of the fracture should each be disposed as a coplanar parallel array with a prescribed spacing between the pins.

The corresponding ends of each set of pins are secured by a respective clamp assembly 30. Each clamp assembly is of the same form and comprises a pair of plates 31 clamped together in mutually facing manner by bolts 32.

The facing surfaces of the plates are provided with parallel grooves 33 in which the bone pin ends seat, and these grooves are preferably formed in respective layers 34 of electrically insulating material fixably secured to the facing surfaces of the plates. Also, the outer surfaces of the plates are provided with outwardly perpendicularly projecting posts 35.

Each post has connected to it a respective coupling assembly 40, of which only four are shown in FIG. 1 to simplify the latter. The assemblies 40 are all the same and each comprise first and second clamps 41 and 42 which are independently operable, rigidly interconnected, and adapted to secure an elongate member in prescribed mutually perpendicular orientations. More particularly in the present embodiment each assembly 40 comprises a rectangular block 43 formed with respective slots 44 from its opposite ends, with these slots being parallel to respectively different pairs of opposite sides of the block. The facing surfaces of these slots are formed across their widths with grooves 45 by drilling the block. The relevant clamping actions are effected by respective bolts 46 acting across the block at the free end portions of the slots beyond the grooves.

It will be seen from FIG. 1 that each post is connected with one clamp of the associated assembly 40 in self-evident manner and, although the two clamps of each assembly 40 can be the same, apart from orientation, these post clamps are conveniently denoted alike as the first clamps 41.

The remaining parts of the apparatus of FIG. 1 are longitudinally adjustable rod mechanisms 50. In practice there will usually be four such mechanisms, but only two are shown for simplicity in FIG. 1. These mechanisms are located in the general direction of the bone 10 and are connected at their ends in the second clamps 42 of assemblies 40, respectively associated with different posts 35, different sides of the fracture, and the same side of the bone 10.

Each mechanism 50 comprises a long rod 51 which has a relatively short portion 52 at one end turned perpendicularly to its remainder, such remainder being formed with a thread extending from its free end. A sleeve 53 is slidably located on the threaded portion of the rod 51 between two nuts 54 engaged with the rod, and the sleeve has a short rod 55 projecting radially therefrom. The long rod portions 52 and short rods 55 are connected with the respective clamps 42.

These clamped rods, and also the posts, can be rendered secure against axial movement out of their clamps by insertion of pins 60, of which one is shown, through their free ends.

The use of the apparatus of FIG. 1 is clearly the same in general terms as the prior apparatus of similar genus insofar as a fractured bone can be manipulated to and stabilised in an overall disposition in which bone fragment union can occur. However, in the present case manipulation of the bone is facilitated once the apparatus is assembled by virtue of the overall geometry and the coupling assemblies. More particularly, it is to be appreciated that loosening of the first clamps 41 allows selective adjustment of the apparatus, and bone fragments therewith, in planes parallel to those of the sets of bone pins and this adjustment can be effected in a controlled manner by appropriate movements of the nuts 53. A corresponding selective adjustment can also be made in a mutually perpendicular plane upon loosening of the second clamps 42. Loosening of the first clamps will also, of course, allow selective adjustments between the two sets of pins by movement in the direction of the posts 35.

While the apparatus of FIG. 1 can be used with existing forms of pins and means for inserting the same, pins and accessories of the forms illustrated by FIGS. 2, 3 and 4 are preferred.

Usually bone pins are of a self drilling form and are inserted individually. However, individual insertion must be very careful and time consuming if a parallel coplanar array is to be achieved. This disadvantage is overcome by using the accessories of FIGS. 2 and 3.

FIG. 2 shows an accessory 70 in the form of a multiple chuck assembly, comprising a gear box 71 from which project three like chucks 72 in a parallel coplanar array, each chuck being coaxially secured with a respective like pinion gear 73 housed in the box 71, the gears 73 being coupled by two like idler gears 74, and the central chuck having a drive shaft 75 projecting therebehind from the box 71. The chucks are spaced in the same manner as the bone pin grooves of the clamp assemblies in FIG. 1, and it is evident that three bone pins can be secured in the chucks and driven simultaneously by a drill connected with the drive shaft.

This chuck assembly is best used with a pin guide such as that of FIG. 3 which serves to retain the pins, when drilled into bone, in the desired array at their free end portions until drilled sufficiently into the bone as to be secure. The illustrated guide is denoted generally as 80 and comprises two strip form plates 81 and 82 which are hinged together at one pair of ends to allow movement to and from an overlying disposition. The plates each have three transverse grooves 83 which register in pairs when the plates overlie to conform pins passing therethrough to the desired array. The plates can be held in their overlying pin-guiding disposition by a catch formed, in this instance, by a T-shaped member 84 hinged by its stem to the free end of one plate, 81, and biassed by a spring 85 so that its stem engages a notch 86 in the free end of the other plate, 82, with the T-bar straddling this other plate.

Also, while any existing suitable form of bone pin can be used, these tend to be of simple and economic form which drill relatively inefficiently, or which are used in association with separate, repeatedly used, more efficient drills. It is preferred that the present apparatus be used with self-drillable bone pins and forms such as that of FIG. 4 are preferred to effect more efficient drilling without undue complication of the pin manufacture. This is of course relevant to a preferred procedure involving simultaneous, multiple drilling.

The pin 90 of FIG. 4 is seen to have a conventional shaft 91 with an enlarged, threaded intermediate portion 92, and a drill bit formation at one end whereat the shaft is reduced in diametrally opposed manner to a flat blade 93. This blade is tapered at its free end to a symmetrical V-shape having an apex angle of about 90° and the end faces of this shape are raked in respectively opposite manner to an angle of about 30°.

It will be noted that the more detailed description of the invention so far has related to the first form thereof referred to in the introductory passages, and it is appropriate now to describe the differences in the second form. FIG. 5 serves this purpose and illustrates in an end view (a), a side view (b), and a perspective view (c) an alternative form of clamp assembly, and FIG. 6 shows such an assembly in use. This alternative assembly is thought to be appropriate particularly to paediatric usage since it can serve to provide a less bulky structure and screen from view the patient/pin interface areas.

The assembly of FIG. 5 is denoted generally as 100 and comprises a plate 101 shaped to conform to a limb portion profile. For this purpose the plate is shaped by bending about a single direction therethrough. In the present instance the plate is triangular in shape and is generally curved about the direction between one apex and an intermediate point on the opposite side.

The assembly further involves three tubular projections 102, 103 and 104 from the convex surface of the plate. The bores of these projections pass through the plate, the projections are preferably normal to the adjoining portion of the plate, and at least two of the projections are mutually perpendicular, with the additional projection suitably being similarly mutually inclined to said two projections. In the present case the projections adjoin the triangular vertices portions of the plate, with the mutually perpendicular projections 102 and 103 adjoining the other two vertices from that relative to which the curvature of the plates is defined.

In use of this alternative assembly, bone pins of screw form, e.g. pins 90, are inserted into a bone, without passing wholly therethrough, by way of the tubular projections which can serve as guides for this purpose and also as clamp sleeves by the provision of grub screws 105. In completing an overall apparatus rod mechanisms, e.g. mechanism can be located between two such clamp assemblies by use of coupling assemblies such as the assemblies in FIG. 1, with the projections 102 and 103 serving as posts. It will be noted that since these posts are mutually perpendicular on each plate, the selective adjustment described above with reference to FIG. 1 is available in this case also.

While the present invention has been described more fully with reference to the illustrated embodiments, the latter are specifically given by way of example, and the invention is capable of variation within the scope of the appended claims. For example, the clamp assemblies of FIG. 1 may have only a single post each, the clamp assembly of FIG. 5 may have a post or posts separate from the tubular projections, and so on.

I claim:

1. Orthopaedic fracture fixation apparatus comprising:

two similar bone pin clamp assemblies respectively to be located proximally and distally with respect to a fracture site in a long bone of a limb;

each said clamp assembly including a plate formed to approximate a curved surface generally conforming to the profile of said limb, and said plate having two spaced tubular projections from its generally convex face to guide individual bone pins clamped therein in predetermined mutually perpendicular directions;

two longitudinally adjustable rod mechanisms, each to extend across said fracture site between a separate pair of said projections, a pair being constituted by one projection from each said clamp assembly;

and four coupling mechanisms, each including a pair of clamps, which clamps are independently operable, are rigidly interconnected, and include two guides respectively to secure elongate members in predetermined mutually perpendicular directions;

each said coupling mechanism being located at a respective one of said projections to secure in said two guides adjacent portions of said one projection and the associated one of said rod mechanisms.

2. Apparatus according to claim 1 wherein said plate is generally triangular and has three said projections respectively from apex portions thereof.

3. Apparatus according to claim 2 wherein said triangular plate is formed to approximate said surface by bending about a direction between one apex portion and an intermediate point of the opposing side, and said projections adjacent the remaining two apex portions are mutually perpendicular.

* * * * *